(12) United States Patent
Rife

(10) Patent No.: US 9,441,755 B2
(45) Date of Patent: Sep. 13, 2016

(54) MULTI CHANNEL VALVE

(71) Applicant: Robert Rife, Mt. Pleasant, SC (US)

(72) Inventor: Robert Rife, Mt. Pleasant, SC (US)

( * ) Notice: Subject to any disclaimer, the term of this patent is extended or adjusted under 35 U.S.C. 154(b) by 122 days.

(21) Appl. No.: 14/205,814

(22) Filed: Mar. 12, 2014

(65) Prior Publication Data

US 2014/0261809 A1  Sep. 18, 2014

Related U.S. Application Data

(60) Provisional application No. 61/781,505, filed on Mar. 14, 2013.

(51) Int. Cl.
*G05D 11/00* (2006.01)
*F16K 31/08* (2006.01)
*F16K 11/02* (2006.01)
*A61M 39/22* (2006.01)

(52) U.S. Cl.
CPC .......... *F16K 31/084* (2013.01); *A61M 39/223* (2013.01); *F16K 11/02* (2013.01); *Y10T 137/2567* (2015.04); *Y10T 137/7904* (2015.04); *Y10T 137/86815* (2015.04)

(58) Field of Classification Search
CPC ............... F16K 31/062; F16K 31/084; Y10T 137/2564; Y10T 137/2567; Y10T 137/7904; Y10T 137/791; Y10T 137/86815; Y10T 137/87676
See application file for complete search history.

(56) References Cited

U.S. PATENT DOCUMENTS

| | | | | |
|---|---|---|---|---|
| 1,675,231 A * | 6/1928 | Stoke | ............................ | 222/205 |
| 3,447,556 A * | 6/1969 | Howeth | ................... | F15B 11/17 137/112 |
| 3,520,319 A * | 7/1970 | McCracken | ............ | F16K 15/04 137/111 |
| 3,552,437 A * | 1/1971 | Blosser, Jr. | ........... | F16K 11/056 137/625.4 |
| 3,900,230 A * | 8/1975 | Durling | ................. | B60T 11/326 128/205.15 |
| 3,945,784 A * | 3/1976 | Collins | .......................... | 425/130 |
| 4,162,146 A * | 7/1979 | Seibert | ............................. | 96/113 |
| 4,275,759 A * | 6/1981 | Huang | ............................ | 137/528 |
| 4,275,823 A * | 6/1981 | Credle, Jr. | ............ | B67D 1/0462 137/113 |
| 4,944,327 A * | 7/1990 | Gyben | ........................ | 137/519.5 |
| 6,092,545 A * | 7/2000 | Bedore | ................. | F16K 31/084 137/102 |
| 6,446,656 B1 * | 9/2002 | Franks | ........................... | 137/112 |
| 7,165,571 B1 * | 1/2007 | Buzdum | ......................... | 137/112 |
| 2008/0041452 A1 * | 2/2008 | Zweber | ............................ | 137/12 |
| 2010/0078083 A1 * | 4/2010 | Coscarella | ..................... | 137/527 |
| 2011/0108141 A1 * | 5/2011 | Pietras et al. | ................. | 137/528 |
| 2012/0241029 A1 * | 9/2012 | Carollo | ........................... | 137/528 |

* cited by examiner

*Primary Examiner* — R. K. Arundale
(74) *Attorney, Agent, or Firm* — B. Craig Killough; Barnwell Whaley Patterson & Helms

(57) ABSTRACT

A valve provides multiple channels that allow alternating, or in some cases, simultaneous, fluid flow functions to a port of an instrument, without the requirement of manual manipulation of the valve by the user. A floating member such as a ball having magnetic affinity for a portion of the valve is positioned in a home, or normal, position by a magnetic field, where it remains until acted on by fluid pressure. The ball in the home position opens other channels of the device. Under fluid pressure in the channel in which the ball's home position is located, the ball is displaced, obstructing at least one of the other channels, while opening the channel to permit a fluid flow through the channel. When the fluid pressure in the channel is terminated, the ball returns to the home position, and other ports are opened.

12 Claims, 2 Drawing Sheets

MULTI CHANNEL VALVE

Applicant claims the benefit of U.S. Provisional Application Ser. No. 61/781,505 filed and received in the U.S. Patent and Trademark Office on Mar. 14, 2013.

FIELD OF THE INVENTION

This invention pertains to medical devices and methods generally, and is more specifically directed to ports and valves that are useful with devices used in medical procedures.

BACKGROUND OF THE INVENTION

Certain medical procedures require the introduction of a multiple devices or materials into the body. For example, a rigid or flexible scope may be used to view biopsy and/or irrigate body cavities, such as the lungs. These instruments may have a port dedicated for the introduction of instruments, as well as gases and fluids, and in some instances, medications. It is desirable to have a valve with multiple ports and channels that allows these functions with minimal manipulation by the user or assistant.

Current methods and devices accomplish the introduction of multiple instruments or materials by connecting, in sequence, an associated conduit or device directly to an existing port of another medical device, or by using a single, or series of, stopcock devices attached to the existing port. Both of these techniques require manipulation of the valve and/or the port by the user or an assistant when changing procedure modalities. Changing connections or manipulating stopcocks or similar valves is cumbersome, and attracts attention away from the medical procedure, increasing the likelihood of error. Stopcocks in current use increase the likelihood of introducing the wrong material if the stopcock is inadvertently placed in the wrong position.

SUMMARY OF THE INVENTION

The present invention provides multiple channels that allow alternating, or in some cases, simultaneous, fluid flow functions to a port of an instrument, without the requirement of manual manipulation of the valve by the user. A floating member such as a ball having magnetic affinity for a portion of the valve is positioned in a home, or normal, position by a magnetic field, where it remains until acted on by fluid pressure. The ball in the home position opens other channels of the device. Under fluid pressure in the channel in which the ball's home position is located, the ball is displaced, obstructing at least one of the other channels, while opening the channel to permit a fluid flow through the channel. When the fluid pressure in the channel is terminated, the ball returns to the home position, and other ports are opened. These ports allow the administration of gas or other fluids or the introduction of tubes or instruments for biopsy or other procedures. The device may also be used post procedure for introducing cleaning agents and cleaning brushes.

BRIEF DRAWING DESCRIPTION

FIG. 1 demonstrates attachment of a multiple channel valve according to an embodiment of the invention to a medical device.

DESCRIPTION OF PREFERRED EMBODIMENTS

Figure 1:
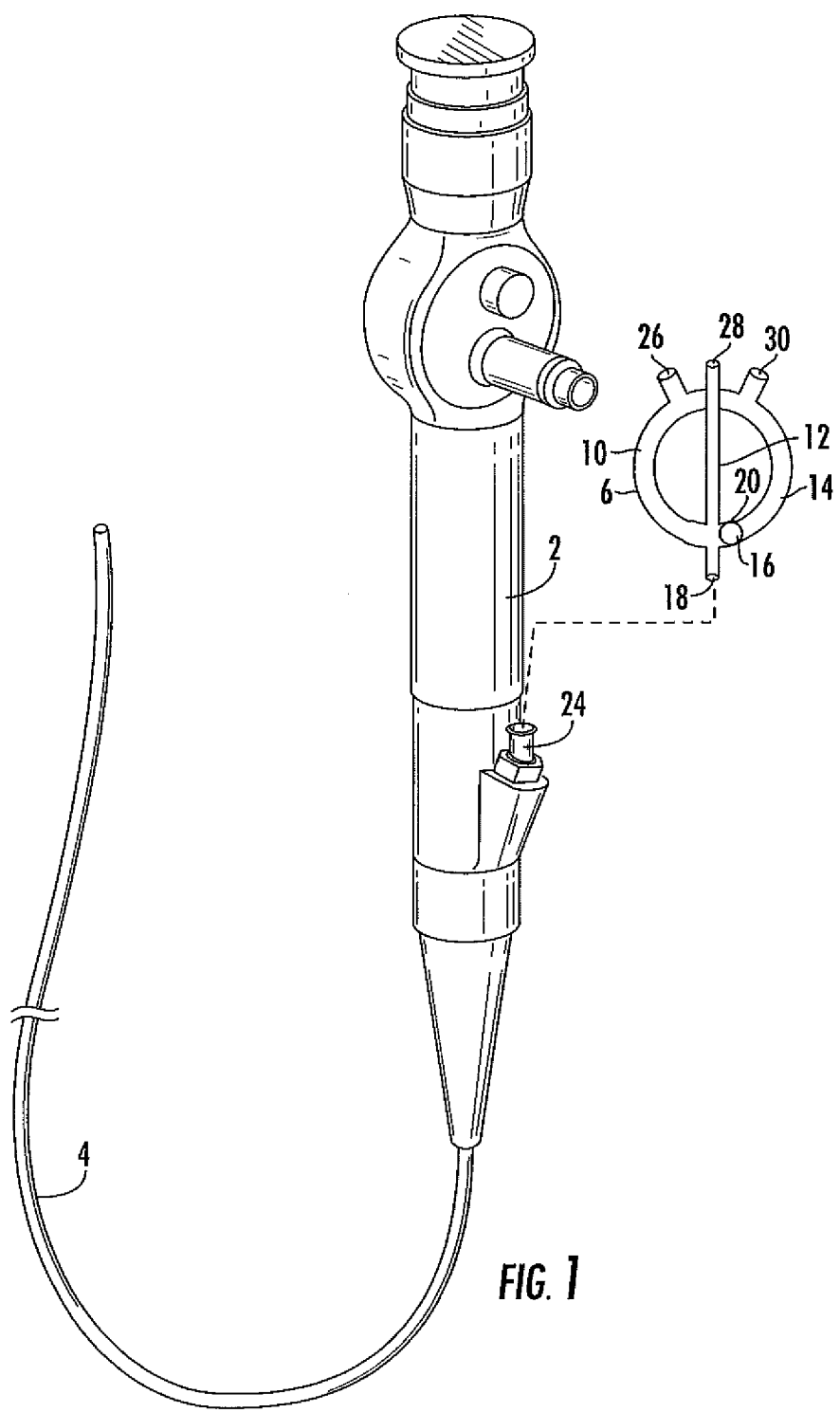

FIG. 1 shows an exemplary medical device 2 of a type that may be used with the invention. The device 2 is a bronchoscope having ports for the introduction of materials or devices. The invention is not limited to use with the exact structure of the device 2 shown in FIG. 1. The invention may be used with medical devices having ports through which multiple objects or fluids or materials are transported. Materials or objects may flow through a lumen 4 that is in communication with, but opposite, the port 24.

Medical devices in common use have ports, such as port 24. Conduits may be connected to the ports. Valve 6 of the present invention is connected to a port. Appropriate fittings are present on the device 2 and/or valve 6 to permit attachment of the valve 6 to, for example, port 24 of the device 2. In one embodiment, a luer fitting is used for attachment of the valve 6 to the device 2. In some embodiments, luer fittings may be used with the ports shown at the top of the valve 6 to connect to fluid sources. The particular fittings for connection of the valve to the device may be chosen according to the application.

In one embodiment, the valve has three channels. Each channel of this embodiment comprises one associated inlet port 26, 28, 30 and a lumen. However, in some applications, materials may flow in both directions through the ports 18, 26, 28, 30.

A third channel, which may be a center channel 12, is preferred to pass straight through, or substantially straight through, the valve. The center channel as shown is useful for passing scopes, or similar mechanical devices, such as forceps or tubes, into, through, and out of the valve 6, without obstruction. The center channel may be used in conjunction with channel 10 or channel 14 to mix fluids at the confluence of the channels, or the center channel may be closed by insertion of a stopper or other obstruction in port 28. The center channel is preferred to communicate with channel 10 and channel 14 only near the lower, outlet port, such as port 18. As shown in the drawings, channel 12 of this embodiment does not communicate with channel 10 or channel 14 near the inlets to the ports 26, 28, 30.

Figure 2:
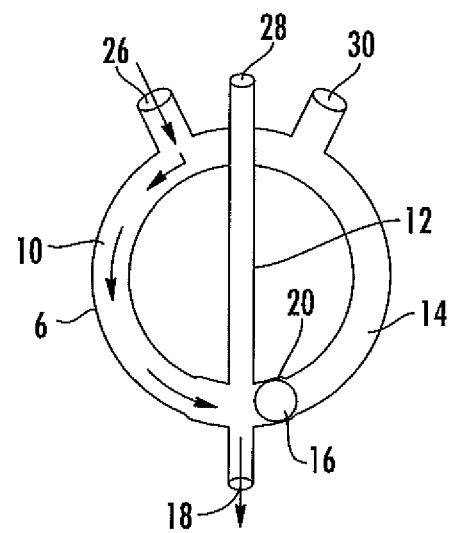
FIG. 2 is an elevation of the multiple channel valve with the ball in the home, or normal, position.

In the embodiment shown in the drawings, a first channel 10 is normally unobstructed. This channel is useful for allowing a flow of fluid, such as a gas, which may be oxygen, through the channel. The fluid may be a liquid. Flow of the fluid may be from port 26 through channel 10 and out of port 18 (FIG. 2), or the direction of flow may be reversed.

In the embodiment shown in the drawings, a second channel 14 is normally obstructed. This channel is useful for allowing a flow of fluid, which may be a liquid or a gas, through the channel. A floating member, such as ball 16, is held in place near a lower opening of the channels by a magnetic field. The ball obstructs the channel, and prevents fluid flow from channel 10 through channel 14, and helps direct fluid flow through port 18 and into the device 2. By floating, it is meant that the floating member moves in or traverses the channels as described herein, and not that the floating member necessarily possesses a propensity to be buoyant in a particular fluid.

The floating member has an affinity for a magnetic field. Accordingly, the ball includes a ferrous component and/or comprises magnetic material. A portion of channel 14 also includes a ferrous component and/or a magnetic field 20, so that the ball is normally held in place at a home position near the lower opening of the channel by magnetic attraction between the portion of the channel and the floating member.

In a preferred embodiment, the home position comprises the magnetic field for the ball. The ball in one embodiment is preferred to be spherical for movement in channels that are preferred to have a generally circular cross section, and the ball may be similar to a ball bearing. The ball is preferred to be resistant to corrosion, and may be an alloy. The ball is preferred to comprise of a resilient material and travel within lumens of the channels that are also resilient so as to provide a better seal of the channels. The ball may be coated in silicone, synthetic rubber, resilient plastics or similar materials.

In use, when fluid pressure in introduced into channel 14, the fluid pressure pushes the ball into the lower end of channel. Fluid flow is demonstrated by the arrows in FIG. 3. Fluid exits the channel and flows through port 18 and flows into a device, such as device 2 through port 24. The ball either fully or partially obstructs channel 10, depending on the design of the channel, and the size of the ball relative to the channel. When fluid pressure in channel is relieved, the ball is attracted by magnetism back to the home position in channel 14, and flow of fluid through channel 10 is restored. The flow of material through channel 14 is again obstructed. The movement of the ball, and the associated opening and closing of channels, is directed by fluid pressure, and manual manipulation of stopcocks or other valve handles is not required.

Figure 3:
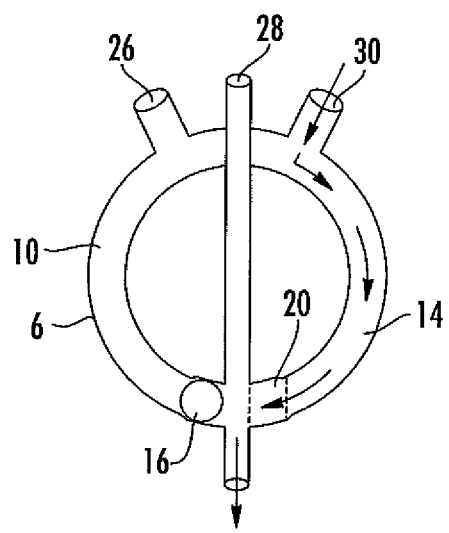
FIG. 3 is another elevation of the multiple channel valve demonstrating repositioning of the ball.

The ball and the channels are constructed and arranged so that the ball is moved from the home position in channel 14 to channel 10 as shown in FIG. 3 without exiting the port 18, such as by being enlarged relative to the channel 12 and port 18. The amount of pressure that is necessary to dislodge the ball from the home position so as to open channel 14 to fluid flow may be designed by increasing the magnetic attraction between the ball and the home position to require greater fluid pressure to open the valve, or decreasing magnetic attraction to lessen the amount of fluid pressure necessary to open the valve.

In a preferred embodiment, the valve is transparent or substantially transparent. Operation of the device can be determined by quick visual observation. The position of a scope or tube or similar object can be seen in channel 12 if that channel is transparent or sufficiently transparent, and the position of the ball and the flow of liquids can be seen in other channels if at least the portion of the valve where the floating member or ball traverses is transparent or sufficiently transparent.

In a preferred embodiment, the lower end of one or both of channels 10, 14 is tapered, such as being slightly frusto-conical, or otherwise has a reduced dimension, including the home position of channel 14. The cross section of channel 10 and/or channel 14 tapers from larger to smaller in the direction away from port 18. This shape restricts movement of the ball, while also providing an increased sealing surface for the ball against the channels 10, 14. The frusto conical portion of the channels may be resilient for improved sealing. The magnetic affinity is constructed and arranged so that the ball is pulled to a stop position against the taper of the channel by the magnet.

The invention provides a valve that does not include switches or other controls that require manual or electrical manipulation. The valve is automatically positioned by the flow of fluids through the channels 10 and 14.

What is claimed is:

1. A valve, comprising:
   a first fluid channel having an inlet port and communicating with an outlet port;
   a second fluid channel having an inlet port and communicating with the outlet port;
   a floating member having a magnetic affinity for a portion of the second fluid channel, the floating member being constructed and arranged to traverse a portion of the first fluid channel and a portion of the second fluid channel;
   wherein, in use, the floating member is normally positioned within the portion of the second fluid channel for which the floating member has the magnetic affinity, and wherein, when fluid pressure is introduced into the second fluid channel, the fluid pressure moves the floating member away from the second fluid channel and to a position that closes fluid flow in the first fluid channel, and wherein when fluid pressure is reduced in the second fluid channel, the floating member returns to the portion of the second fluid channel for which the floating member has the magnetic affinity.

2. The valve as described in claim 1, wherein the floating member is spherical in shape, and wherein a cross section of a portion of a lumen of the first fluid channel and a cross section of a portion of a lumen of the second fluid channel traversed by the floating member are generally circular.

3. The valve as described in claim 1, wherein the floating member is spherical in shape, and wherein a cross section of a portion of a lumen of the first fluid channel and a cross section of a portion of a lumen of the second fluid channel traversed by the floating member are generally circular, and a cross section of a second portion of the first fluid channel and a cross section of a second portion of the second fluid channel traversed by the floating member each have generally frusto conically shaped lumens.

4. The valve as described in claim 1, further comprising a third channel that communicates with the first fluid channel and the second fluid channel at a lower end of the valve near the outlet port.

5. The valve as described in claim 1, further comprising a third channel, the third channel comprising a lumen, an inlet and an outlet that are in a substantially straight alignment with each other.

6. The valve as described in claim 1, wherein the portion of the valve in which the floating member traverses is substantially transparent.

7. The valve as described in claim 1, wherein the first fluid channel is normally open and unobstructed from the inlet port to the outlet port.

8. The valve as described in claim 1, wherein an inside diameter of the first fluid channel in which the floating member is received when the fluid pressure moves the floating member to a position that obstructs fluid flow in the first fluid channel is larger than an adjacent inside diameter of the first fluid channel.

9. The valve as described in claim 1, wherein an inside diameter of the portion of the second fluid channel that has the magnetic affinity for the floating member is larger than an adjacent inside diameter of the second fluid channel.

10. The valve as described in claim 1, further comprising a third channel.

11. The valve as described in claim 1, wherein the floating member comprises a magnetic component.

12. The valve as described in claim 1, wherein the portion of the second fluid channel for which the floating member has a magnetic affinity comprises a magnetic component.

* * * * *